(12) United States Patent
Korte et al.

(10) Patent No.: US 9,018,144 B2
(45) Date of Patent: Apr. 28, 2015

(54) POLYMER COMPOSITION, SWELLABLE COMPOSITION COMPRISING THE POLYMER COMPOSITION, AND ARTICLES INCLUDING THE SWELLABLE COMPOSITION

(75) Inventors: James R. Korte, Katy, TX (US); John Thurston, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 545 days.

(21) Appl. No.: 12/636,176

(22) Filed: Dec. 11, 2009

(65) Prior Publication Data

US 2010/0147507 A1 Jun. 17, 2010

Related U.S. Application Data

(63) Continuation-in-part of application No. 12/242,338, filed on Sep. 30, 2008, now Pat. No. 8,181,708.

(60) Provisional application No. 60/976,575, filed on Oct. 1, 2007.

(51) Int. Cl.
| | |
|---|---|
| *C09K 8/42* | (2006.01) |
| *C09K 8/50* | (2006.01) |
| *A61L 24/04* | (2006.01) |
| *A61L 24/10* | (2006.01) |
| *A61L 27/34* | (2006.01) |
| *C08L 9/02* | (2006.01) |
| *C08L 21/00* | (2006.01) |
| *C08L 31/02* | (2006.01) |
| *C08L 33/00* | (2006.01) |
| *C08L 33/06* | (2006.01) |
| *C08L 33/26* | (2006.01) |
| *E21B 33/12* | (2006.01) |
| *C08L 91/00* | (2006.01) |
| *C08K 3/00* | (2006.01) |
| *C08K 5/01* | (2006.01) |
| *C08L 33/08* | (2006.01) |
| *C08L 33/20* | (2006.01) |

(52) U.S. Cl.
CPC ............... *C09K 8/50* (2013.01); *A61L 24/043* (2013.01); *A61L 24/106* (2013.01); *A61L 27/34* (2013.01); *A61L 2420/04* (2013.01); *C08K 3/0033* (2013.01); *C08K 5/01* (2013.01); *C08L 9/02* (2013.01); *C08L 21/00* (2013.01); *C08L 31/02* (2013.01); *C08L 33/00* (2013.01); *C08L 33/06* (2013.01); *C08L 33/08* (2013.01); *C08L 33/20* (2013.01); *C08L 33/26* (2013.01); *C08L 2205/03* (2013.01); *E21B 33/1208* (2013.01); *C08L 91/00* (2013.01)

(58) Field of Classification Search
CPC .............. C09K 8/52; C09K 3/32; C09K 8/58; C09K 2208/28; C09K 8/035; C09K 8/28; C09K 8/602; C09K 8/68; C09K 8/805; C09K 2205/22; C09K 2205/34; C09K 2205/40; C09K 2208/04; C09K 2208/08; C09K 2208/30
See application file for complete search history.

(56) References Cited

U.S. PATENT DOCUMENTS

| | | | | |
|---|---|---|---|---|
| 4,110,529 | A * | 8/1978 | Stoy | 528/491 |
| 4,590,227 | A | 5/1986 | Nakamura et al. | |
| 6,169,058 | B1 | 1/2001 | Le et al. | |
| 6,358,580 | B1 * | 3/2002 | Mang et al. | 428/35.7 |
| 6,365,656 | B1 * | 4/2002 | Green et al. | 524/313 |
| 6,681,849 | B2 | 1/2004 | Goodson, Jr. | |
| 6,848,505 | B2 | 2/2005 | Richard et al. | |
| 7,059,415 | B2 | 6/2006 | Bosma et al. | |
| 7,143,832 | B2 | 12/2006 | Freyer | |
| 2005/0171248 | A1 | 8/2005 | Li et al. | |
| 2005/0209382 | A1 * | 9/2005 | Yale et al. | 524/379 |
| 2007/0012447 | A1 | 1/2007 | Fang et al. | |
| 2007/0056735 | A1 | 3/2007 | Bosma et al. | |
| 2007/0244225 | A9 * | 10/2007 | Sutherland | 523/336 |
| 2009/0084550 | A1 | 4/2009 | Korte et al. | |
| 2009/0131563 | A1 | 5/2009 | Wang et al. | |

FOREIGN PATENT DOCUMENTS

| | | |
|---|---|---|
| CA | 2662945 A1 | 3/2008 |
| CA | 2677254 A1 | 8/2008 |
| WO | 2010039131 A1 | 4/2010 |

OTHER PUBLICATIONS http://en.wikipedia.org/w/index.php?title=Mineral_oil&printable=yes downloaded on Jul. 23, 2014.*
International Search Report; International Application No. PCT/US2010/059478; International Filing Date: Dec. 8, 2010; Date of Mailing: Aug. 19, 2011; 6 pages.
Written Opinion of the International Searching Authority; International Application No. PCT/US2010/059478; International Filing Date: Dec. 8, 2010; Date of Mailing: Aug. 19, 2011; 5 pages.
J. Goodson et al., "Effect of Salt Type, Concentration and Temperature on Water Swelling Packer Compound," Proceedings: Oilfield Engineering with Polymers 2008, Oct. 7-8, 2008, Session 2, Cavendish Conference, London, UK, pp. 1-8.

(Continued)

*Primary Examiner* — Susannah Chung
*Assistant Examiner* — Kumar R Bhushan
(74) *Attorney, Agent, or Firm* — Cantor Colburn LLP

(57) ABSTRACT

A polymer composition includes a base polymer comprising a hydrocarbon rubber, an acrylic copolymer, and a refined oil in which the acrylic polymer is dispersed. The polymer composition is swellable when treated with an aqueous medium, non-aqueous medium, or both. A sealing element for a flow channel includes an expandable section filled with a swellable composition that swells when treated with a swelling material. The swellable composition includes the polymer composition, and the swelling material may be aqueous, non-aqueous, or both.

19 Claims, 2 Drawing Sheets

(56) References Cited

OTHER PUBLICATIONS

The Free Library, [online]; retrieved on Jan. 10, 2010]; retrieved from the Internet http://www.thefreelibrary.com/_/print/PrintArticle.aspx?id=179241932 P. McElfresh et al.,"Studie of water Swellable NBR for downhole sealing applications", Rubber World, May 1, 2008, 5 pages, without figures.

P. McElfresh et al.; "Studies of Water Swellable NBR for Downhole Sealing Applications," Rubber World, May 1, 2008, available without Figures from http://www.thefreelibrary.com/_/print/Pr9intArticle.aspx?id=179241932.

J. Goodson et al.; "Effect of Salt Type, Concentration and Temperature on Water Swelling Packer Compound," Proceedings: Oilfield Engineering with Polymers 2008, Oct. 7-8, 2008, Session 2, Cavendish Conference, London, UK, pp. 1-8.

Canadian Office Action for related Canadian Application No. 2,835,959, dated Feb. 4, 2014, pp. 1-2.

* cited by examiner

POLYMER COMPOSITION, SWELLABLE COMPOSITION COMPRISING THE POLYMER COMPOSITION, AND ARTICLES INCLUDING THE SWELLABLE COMPOSITION

CROSS REFERENCE TO RELATED APPLICATION

This application is a continuation-in-part of copending U.S. application Ser. No. 12/242,338, filed Sep. 30, 2008 which is a non provisional of U.S. Application No. 60/976,575, filed Oct. 1, 2007, which is incorporated herein by reference.

BACKGROUND OF THE INVENTION

In downhole drilling and completion industries, it is frequently necessary to seal the annular space between a borehole wall and a tubular therewithin. Such sealing can be accomplished by a number of different sealing mechanisms including swellable seals.

One example of swellable seals in the art is known commercially as a Reactive Element Packer or REPacker™ reactive element packer, available from Baker Oil Tools, Houston Tex. REPackers are commercial isolation tools that use elastomer swelling technology to provide a barrier in surrounding member/open hole and surrounding member/surrounding member annuli. Such packers may have a water reactive section, an oil reactive section, or both. A water reactive section may include water-absorbing particles incorporated in nitrile-based polymer. These particles swell via absorbing water, which in turn expands the rubber without being physically absorbed into the rubber matrix, which can adversely affect properties. Similarly, an oil reactive section may include hydrocarbon-absorbing rubbers and polymers, in which uptake of the hydrocarbon by the polymer causes swelling and lubricates and decreases the mechanical strength of the polymer chain as it expands.

However, under certain circumstances, it may be impractical to deploy a seal or packer having one or the other of a water or oil swellable section based on availability of swelling material, or other considerations including environmental considerations. The art would well receive seals responsive to a wider variety of swelling materials, while maintaining or increasing the swelling ability and effectiveness of the swelled material.

SUMMARY

The above disadvantages are overcome by, in an embodiment, a polymer composition including a base polymer comprising a hydrocarbon rubber, an acrylic copolymer, and a refined oil in which the acrylic polymer is dispersed. The polymer composition is swellable when treated with an aqueous medium, non-aqueous medium, or both.

In another embodiment, a sealing element for a flow channel includes an expandable section filled with a swellable composition that swells when treated with a swelling material.

In another embodiment, a method of sealing a well hole includes inserting the sealing element into a well, and introducing a swelling material into the expandable section.

We turn now to the figures, which are meant to be exemplary of the embodiments and not limited thereto.

Figure 1:
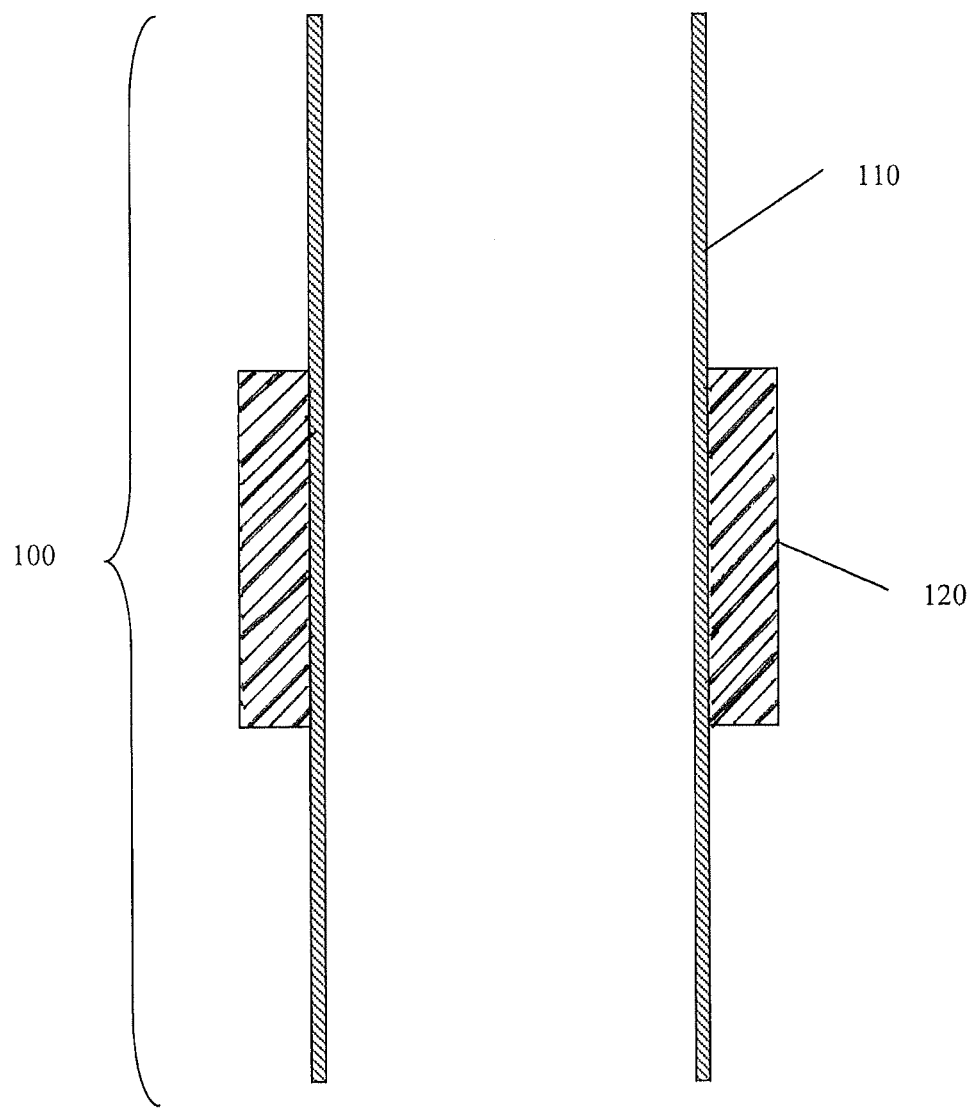
FIG. 1 is a cross-sectional schematic view of an exemplary annular sealing element.

The above described and other features are exemplified by the following detailed description.

DETAILED DESCRIPTION OF THE INVENTION

It has surprisingly been found that a polymer composition for a swellable composition, which combines an oil swellable base polymer and an acrylic polymer dispersion in a refined oil, can be swelled by treatment of the polymer composition with either an aqueous medium, non-aqueous medium, or both (e.g., wellbore fluids such as water, brine, hydrocarbons, drilling mud, or a combination of these).

The polymer composition includes an oil swellable base polymer, an acrylate copolymer, and a refined oil. As used herein, the terms "refined oil" each refers to a petroleum distillate fraction of hydrocarbons of 15 to 40 carbon atoms. The refined oil may be aromatic or non-aromatic. A useful base polymer is a hydrocarbon rubber which swells in the presence of refined oils. Hydrocarbon rubbers, such as those embodied herein, may include those based on elastomeric diene monomers such as 1,3-butadiene or isoprene (as found in natural rubbers), and may be homo- or copolymers.

The base polymer may also be a copolymer. It will be understood that unless otherwise noted herein, the term "polymer" comprises polymers of one monomer, copolymers, terpolymers and polymeric forms of more than one type of monomer. It will also be understood in general that the term "copolymer", as used herein, may indicate the presence of two or more monomers, and may therefore also encompass the terms terpolymer, tetrapolymer, pentapolymer, and the like, and therefore the terms polymer and copolymer should not be construed as limiting to the use of only one or two monomers respectively, unless otherwise specified. Where "terpolymer", is used herein, this term refers to the presence of three monomers in the polymer unless otherwise specified.

The base polymer may be a random or block copolymer. Where a random copolymer is used, the monomers are substantially randomly dispersed in the polymer. Where a block copolymer is used, the block copolymer may be a diblock copolymer, a triblock copolymer, a diblock terpolymer, or the like. It will be understood that each block may be a homopolymer or random copolymer.

In an embodiment, the oil swellable base polymer comprises polyethylenes, polypropylenes, poly(ethylene-co-propylene), polyamides, polyesters, polyurethanes, polyvinylchlorides, and rubbers such as ethylene-propylene-diene monomer (EPDM) rubber, butadiene rubber, styrene-butadiene rubber, butyl rubber, natural rubber, or a combination comprising at least one of the foregoing. In a specific embodiment, the base polymer is ethylene-propylene-diene monomer (EPDM) rubber, butadiene rubber, styrene-butadiene rubber, butyl rubber, natural rubber, or a combination comprising at least one of the foregoing. In an exemplary embodiment, the base polymer is EPDM.

The polymer composition also includes an acrylic copolymer of hydrophilic acrylic monomers. A dispersion of such a polymer in a medium, such as in a refined oil or oil/water emulsion, is also referred to herein as a liquid dispersed polymer (LDP). A useful acrylic copolymer for an LDP includes an acidic monomer such as, for example, acrylic acid, methacrylic acid, itaconic acid, maleic acid, fumaric acid, or a combination comprising at least one of these. In an embodiment, the acidic monomer is acrylic acid or methacrylic acid.

The acrylic copolymer also includes a polar hydrophilic monomer, and in particular, an amide monomer. Exemplary amide monomers include acrylamide; N-alkyl acrylamides such as N-methylacrylamide, N,N-dimethylacrylamide, N-ethylacrylamide, N,N-diethylacrylamide, or N-hydroxyethylacrylamide; methacrylamide; N-alkyl methacrylalmides such as N-methylmethacrylamide, N,N-dimethylmethacrylamide, N-ethylmethacrylamide, N,N-diethylmethacrylamide, N-hydroxyethylmethacrylamide, or N,N-dihydroxyethylmethacrylamide; maleimide; N-alkylmaleimides such as N-methylmaleimide, N-ethylmaleimide, N-phenylmaleimide, and the like; or a combination comprising at least one of the foregoing. In an embodiment, the amide monomer is acrylamide or methacrylamide.

The acrylic copolymer includes the acidic monomer and the amide monomer in a weight ratio of 99:1 to 1:99, specifically 95:5 to 5:95, and more specifically 90:10 to 10:90.

In an embodiment, the acrylic copolymer consists essentially of the acidic monomer and the amide monomer. In another embodiment, the acrylic copolymer consists of the acidic monomer and amide monomer. The acrylic copolymer may be a solution polymerized copolymer, but is typically an emulsion or suspension polymerized polymer. In a specific embodiment, the acrylic copolymer is an aqueous emulsion polymer having a polymer solids content of 40 to 99 wt %, specifically 45 to 95 wt %, and more specifically 50 to 90 wt %, based on the total weight of the aqueous emulsion polymer.

In a specific embodiment, the acrylic copolymer comprises at least one of acrylic acid and methacrylic acid, and at least one of acrylamide and methacrylamide. In an exemplary embodiment, the acrylic copolymer is a copolymer of acrylic acid and acrylamide. An example of a commercial acrylic copolymer is DPNT06-0124 which is an acrylic acid/acrylamide copolymer dispersion in heavy petroleum naphtha, commercially available from Ciba Corporation.

Additional monomers copolymerizable with the acidic and amide monomers may be included provided the inclusion of these monomers does not significantly adversely affect the desired properties of the swellable composition. Additional monomers that may be included in the acrylic copolymer include, but are not limited to, polar acrylate or acrylic monomers such as those having nitrile functional groups including acrylonitrile, methacrylonitrile, 2-cyanoethylacrylate, 2-cyanoethylmethacrylate, and the like; aldehydic monomers such as acrolein, methacrolein, and the like; hydroxy-containing monomers such as 2-hydroxyethyl acrylate (HEA), 2-hydroxyethyl methacrylate (HEMA), 2-hydroxypropylacrylate, 2-hydroxypropylmethacrylate, and the like; anhydrides such as maleic anhydride, itaconic anhydride, and the like; nonpolar acrylate monomers such as methyl acrylate, methyl methacrylate, ethyl acrylate, ethyl methacrylate, n-propyl acrylate, propyl methacrylate, n-butyl acrylate, n-butyl methacrylate, isobutyl acrylate, isobutyl methacrylate, t-butyl acrylate, pentyl acrylate, hexyl acrylate, cyclohexyl acrylate, n-octyl acrylate, and the like; aromatic monomers including styrene, alpha-methylstyrene, phenyl acrylate, phenyl methacrylate, benzyl acrylate, benzyl methacrylate, and the like; or a combination comprising at least one of the foregoing. Typical additional monomers, where used, may include HEA, HEMA, 2-hydroxypropyl methacrylate, ethyl acrylate, methyl methacrylate, n-butyl acrylate, and styrene.

The additional monomers, where included, may be used in an amount of less than or equal to 80 wt %, specifically less than 70 wt %, and more specifically less than 50 wt %, based on the total weight of acidic monomer, amide monomer, and additional monomer in the acrylic copolymer.

Cross-linking monomers may also be included. Such cross linking monomers may include, for example, divinyl benzene, ethylene diacrylate, ethylene dimethacrylate, trimethylolpropane triacrylate, trimethylolpropane trimethacrylate, and the like, or a combination comprising at least one of the foregoing. Where included, crosslinkers may be used in amounts of less than or equal to 5 wt %, specifically less than or equal to 2 wt %, and more specifically less than or equal to 1 wt %, based on the total weight of acidic monomer, amide monomer, and additional monomer in the acrylic copolymer.

Alternatively, or in addition, the acrylic copolymer may include combinations of copolymers of acrylic acid and its esters with other materials such as sodium hydroxide, polyacrylamide copolymer, ethylene maleic anhydride copolymer, crosslinked carbomethoxycellulose, polyvinyl alcohol copolymers, cross linked polyethylene oxide, or a combination comprising at least one of the foregoing.

The acrylic copolymer has a weight average molecular weight of 1,000 to 500,000 g/mol, specifically 10,000 to 300,000 g/mol, and more specifically 20,000 to 100,000 g/mol.

The acrylic copolymer may be included in the swellable composition as a suspension in a solvent (e.g., a refined oil as discussed below), as an aqueous emulsion, or may be a mixture of an aqueous emulsion with a refined oil, referred to as discussed hereinabove as an LDP.

The swellable composition thus further includes a refined oil in which the base polymer and the acrylic polymer are dispersed. The refined oil is as described herein a petroleum distillate fraction and may be any $C_{15-40}$ petroleum fraction useful for swelling the base polymer, where the refined oil has a high affinity for the base polymer and for which the base polymer has a high capacity. As used herein, the term "high capacity" with respect to the base polymer is where the base polymer can absorb up to 200 phr, specifically 100 to 150 phr, of refined oil based on 100 parts of base polymer and any added fillers. The refined oil may be a naphthenic oil comprising mostly cycloalkanes and having an n-alkane (paraffin) content of less than about 55-60%; a paraffinic oil (sometimes referred to as a heavy naphtha) having an n-alkane content of greater than about 55-60%; an aromatic oil, such as a phthalate oil derived from phthalic anhydride, and including such compounds as, for example di-n-butylphthalate; or a combination comprising at least one of the foregoing. Of these, it is more desirable to use refined oils that are non-aromatic.

In an embodiment, the refined mineral oil is a phthalate oil, a naphthenic oil, a paraffinic oil, or a combination comprising at least one of the foregoing oils. In a specific embodiment, the refined oil is a naphthenic oil, a paraffinic oil, or a combination comprising at least one of the foregoing oils. Also in an embodiment, the acrylic copolymer is dispersed in the refined oil to prepare the LDP. In an embodiment, the amount of acrylic copolymer dispersed in refined oil is 20 to 80 wt %, specifically 30 to 70 wt %, and more specifically 40 to 60 wt %, based on the total weight of the acrylic copolymer and refined oil.

The acrylic copolymer (as an LDP) is included in the swellable composition in an amount of 30 to 200 parts by weight per 100 parts (also referred to as parts per hundred, abbreviated "phr") by weight (also referred to as parts per hundred, abbreviated "phr") of the base polymer. In an embodiment, the acrylic copolymer is included in an amount of 40 to 180 phr, more specifically 50 to 150 phr, and still more specifically 80 to 140 phr, based on 100 parts of the base polymer.

The swelling composition may further include, in addition to the polymer composition, ingredients or components to provide other performance aspects of the swellable composition. In addition to the base polymer, acrylic copolymer, and refined oil discussed above, these additional ingredients/components include fillers, activators, antioxidants, process aids, and curatives.

There are various other grades of fillers which may be used alone or in combination, and in lesser or greater amounts that may yield comparable, desirable or improved rubber properties. Suitable fillers include, but are not necessarily limited to, carbon black, silica (silicon dioxide, $SiO_2$), clays, calcium carbonate, bentonite, and the like, and combinations thereof. The proportion of filler may range between about 30 and 100 phr.

Suitable activators include, but are not necessarily limited to, magnesium oxide (MgO), zinc oxide (ZnO), zinc stearate, stearic acid and the like and combinations thereof. The proportion of activator may be in the range from about 1-10 phr.

Suitable antioxidants include, but are not necessarily limited to, any of the diphenyl amines (e.g. NAUGARD® antioxidants available from Chemtura Corporation), or any of the mercaptobenzimidazoles (e.g., VANOX® ZMTI from RT Vanderbilt) and the like and combinations thereof.

Suitable process aids include, but are not necessarily limited to, waxes (e.g. VANFRE® waxes available from R. T. Vanderbilt Company), or process aids such as WB-16 process additive from Strucktol, and the like, and combinations thereof. The antioxidants and the process aids may each be in the range of from about 0.5 to about 5.0 phr.

In an exemplary embodiment, a swelling composition may include 100 phr base polymer (e.g., EPDM), 30 to about 200 phr acrylic copolymer, 0.2 to 15 phr curative, 20 to 100 phr carbon black filler, 20 to 100 phr silica filler, 1 to 10 phr activator, 0.5 to about 5 phr antioxidant, and 0.5 to 5 phr process aid.

The polymer composition, and a swelling composition prepared therefrom, may be swelled by treatment by an aqueous swelling material such as water or brine, or by treatment with a non-aqueous swelling material, such as a hydrocarbon as described above, drilling mud, or a combination of these.

It has been found that including the polymer composition disclosed herein in a swellable composition provides a swelling capacity for the swelling composition comparable to that of swelling compositions which only swell under either aqueous or non-aqueous conditions, but not both. The swelling composition disclosed herein may achieve a swelling capacity for the combination of base polymer (e.g., EPDM) and acrylic copolymer in refined oil or water of over 500 volume %. The amount of swelling achieved and the rate of swelling depends on physical boundaries and limitations, the viscosity of the refined oil, the salinity of the water, and the temperature. The lower the concentration of mono-valent salts (e.g. NaCl, KCl) or co-valent salts (e.g., $CaCl_2$), the lower the salinity, and the faster the rate of swelling and the more swelling that can be achieved.

The polymer composition described herein, and the swelling composition prepared therefrom, may be used in a sealing element for a flow channel. In an embodiment, an exemplary sealing element is shown in FIG. 1, in which the sealing element 100 includes a channel 110, and an expandable section 120. The sealing element 100 may be annular in design and surrounding the channel 110, or may be of another shape depending on the application. The sealing element 120 comprises an expandable section 120 filled with a swellable composition (not shown) which includes the polymer composition described herein, which swells when treated with a swelling material. The swelling material may be a wellbore fluid including an aqueous medium such as water or brine, a non-aqueous medium such as hydrocarbons, drilling mud, or a combination comprising at least one of the foregoing.

The expandable sealing element is changeable in shape and size, so that the sealing element may upon expanding conform to the shape and dimensions of the environment in which it is inserted (such as a borehole, well, or the like).

Figure 2:
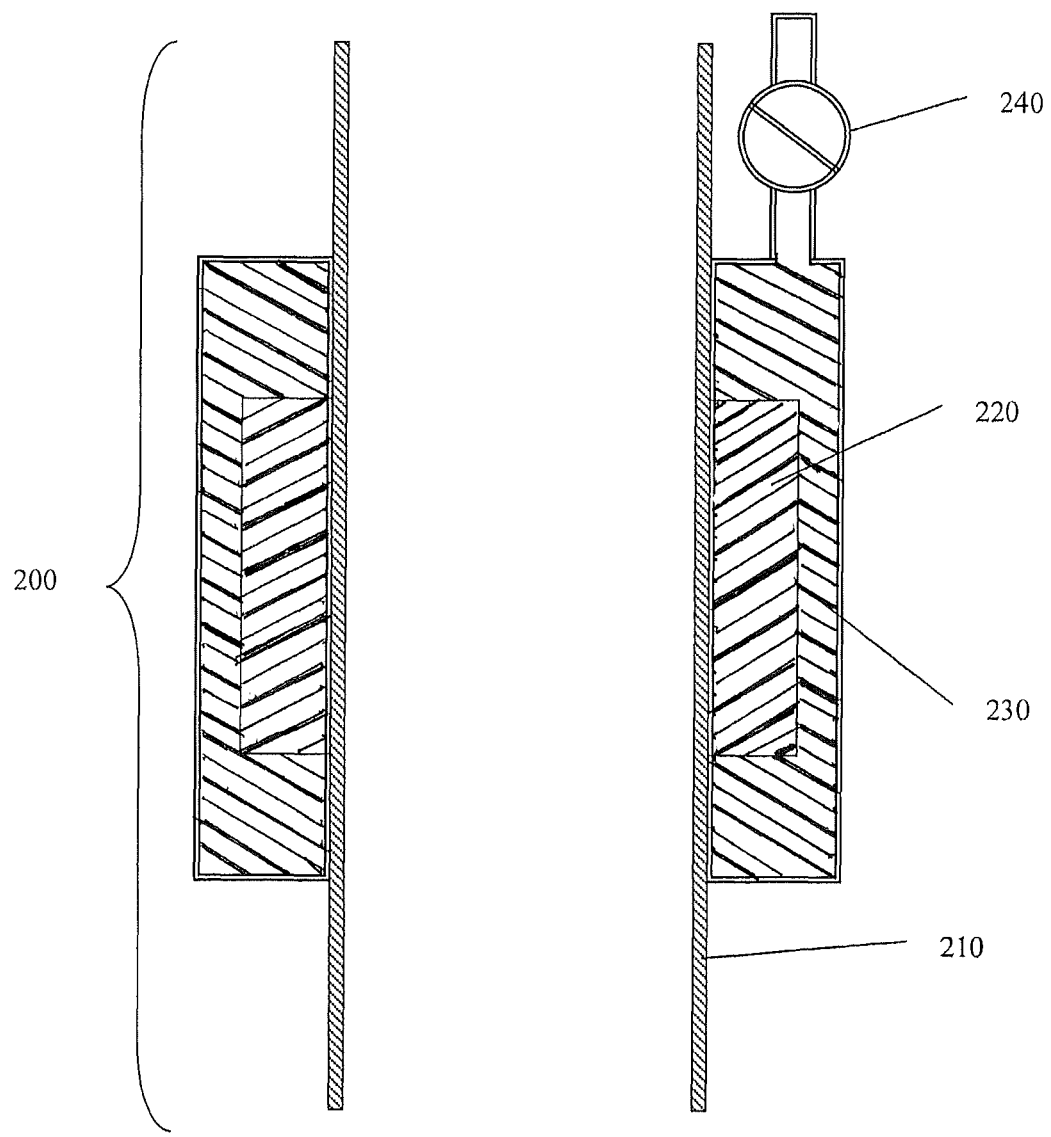
FIG. 2 is a cross-sectional schematic view of a packer having an annular sealing element and an inlet valve.

In another exemplary embodiment, an annular sealing element is included in the structure of a packer and has a through hole running lengthwise through the expandable sealing element containing the swelling material. An exemplary packer is shown in FIG. 2, in which the packer 200 includes a channel 210, an annular expandable section 220, a surrounding member 230 surrounding the channel 210 to encase the expandable section 220. In an embodiment, a valve 240 opens into surrounding member 230 to allow introduction of a swelling material to contact expandable section 220. In this embodiment, the expandable section 220 of the packer 200 conforms by expanding radially outward, to conform to the outer environment, as well as expanding radially toward the center, to constrict around a production pipe or conduit (not shown) inserted through channel 210 the packer. In another embodiment (not shown), the sealing element is a bridge plug for sealing off a bore hole completely, and does not include a hole running through the expandable section.

An exemplary method of sealing a well hole using the sealing element includes inserting the sealing element into a hole (bore hole or well), and introducing a swelling material into the expandable section. The swelling material may be introduced to the sealing element through a tube or line for introducing the swelling material affixed to a valve attached to the surrounding member.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

All ranges disclosed herein are inclusive of the endpoints, and the endpoints are independently combinable with each other.

The use of the terms "a" and "an" and "the" and similar referents in the context of describing the invention (especially in the context of the following claims) are to be construed to cover both the singular and the plural, unless otherwise indicated herein or clearly contradicted by context. The modifier "about" used in connection with a quantity is inclusive of the stated value and has the meaning dictated by the context (e.g., it includes the degree of error associated with measurement of the particular quantity).

The invention claimed is:

1. A polymer composition comprising:
   a base polymer comprising polyethylenes, polyproplenes, poly(ethylene-co-propylene), polyamides, polyesters, polyurethanes, polyvinylchlorides, ethylene-propylene-diene monomer rubber, butadiene rubber, styrene-butadiene rubber, natural rubber, or a combination comprising at least one of the foregoing;

an acrylic copolymer comprising an acidic monomer and an amide monomer present in a weight ratio of 95:5 to 5:95 wherein the acrylic copolymer is present in an amount of 30 to 200 parts by weight per hundred parts by weight of the base polymer; and a refined oil in which the acrylic copolymer is dispersed in the refined oil to form a liquid dispersed polymer, wherein the refined oil comprises a $C_{15-40}$ petroleum distillate fraction; and wherein the polymer composition is swellable when treated with an aqueous medium, non-aqueous medium, or both.

2. The polymer composition of claim 1, wherein the acidic monomer is acrylic acid or methacrylic acid, and the amide monomer is acrylamide or methacrylamide.

3. The polymer composition of claim 2, wherein the acrylic copolymer is a copolymer of acrylic acid and acrylamide.

4. The polymer composition of claim 1, wherein the refined oil is a naphthenic oil, a paraffinic oil, or a combination comprising at least one of the foregoing.

5. The polymer composition of claim 1, wherein the acrylic copolymer is included in the refined oil in an amount of 20 to 80 wt% based on the total weight of the acrylic copolymer and the refined oil.

6. A swellable composition comprising the polymer composition of claim 1, the swellable composition further comprising fillers, activators, antioxidants, process aids, and curatives.

7. The swellable composition of claim 6, comprising 100 phr base polymer, 30 to 200 phr acrylic copolymer, 0.2 to 15 phr curative, 20 to 100 phr carbon black filler, 20 to 100 phr silica filler, 1 to 10 phr activator, 0.5 to about 5 phr antioxidant, and 0.5 to 5 phr process aid.

8. A polymer composition comprising:
  a base polymer comprising polyethylenes, polypropylenes, poly(ethylene-co-propylene), polyamides, polyesters, polyurethanes, polyvinylchlorides, ethylene-propylene-diene monomer rubber, butadiene rubber, styrene-butadiene rubber, natural rubber, or a combination comprising at least one of the foregoing; and
  a liquid dispersed acrylic copolymer, the acrylic copolymer comprising an acidic monomer and an amide monomer present in a weight ratio of 95:5 to 5:95 wherein the acrylic copolymer is present in an amount of 30 to 200 parts by weight per hundred parts by weight of the base polymer,
  wherein the polymer composition is swellable when treated with an aqueous medium, non-aqueous medium, or both.

9. The polymer composition of claim 8, wherein the acidic monomer is acrylic acid or methacrylic acid, and the amide monomer is acrylamide or methacrylamide.

10. The polymer composition of claim 9, wherein the acrylic copolymer is a copolymer of acrylic acid and acrylamide.

11. The polymer composition of claim 8, wherein the liquid dispersed acrylic copolymer comprises a refined oil which comprises a naphthenic oil, a paraffinic oil, or a combination comprising at least one of the foregoing.

12. The polymer composition of claim 8, wherein the liquid dispersed acrylic copolymer comprises an acrylic copolymer dispersed in a refined oil, the acrylic copolymer being present in an amount of 20 to 80 wt% based on the total weight of the acrylic copolymer and the refined oil.

13. A swellable composition comprising the polymer composition of claim 8, the swellable composition further comprising fillers, activators, antioxidants, process aids, and curatives.

14. The swellable composition of claim 13, comprising 100 phr base polymer, 30 to 200 phr acrylic copolymer, 0.2 to 15 phr curative, 20 to 100 phr carbon black filler, 20 to 100 phr silica filler, 1 to 10 phr activator, 0.5 to about 5 phr antioxidant, and 0.5 to 5 phr process aid.

15. The swellable composition of claim 8, wherein the acid monomer comprises acrylic acid, methacrylic acid, itaconic acid, maleic acid, fumaric acid, or a combination comprising at least one of the foregoing; and the amide monomer comprises acrylamide;
  N-methylacrylamide, N,N-dimethylacrylamide, N-ethylacrylamide, N,N-diethylacrylamide, N-hydroxyethylacrylamide, methacrylamide, N-methylmethacrylamide, N,N-dimethylmethacrylamide, N-ethylmethacrylamide, N,N-diethylmethacrylamide, N-hydroxyethylmethacrylamide, N,N-dihydroxyethylmethacrylamide, maleimide, N-methylmaleimide, N-ethylmaleimide, N-phenylmaleimide, or a combination comprising at least one of the foregoing.

16. The polymer composition of claim 8, wherein the acrylic copolymer is present in an amount of 40 to 180 parts by weight per hundred parts by weight of the base polymer.

17. A polymer composition comprising:
  a base polymer comprising polyethylenes, polypropylenes, poly(ethylene-co-propylene), polyamides, polyesters, polyurethanes, polyvinylchlorides, ethylene-propylene-diene monomer rubber, butadiene rubber, styrene-butadiene rubber, natural rubber, or a combination comprising at least one of the foregoing; and
  a liquid dispersed acrylic copolymer comprising an acrylic copolymer dispersed in a refined oil comprising a naphthenic oil, a paraffinic oil, or a combination comprising at least one of the foregoing, the acrylic copolymer being present in an amount of 20 to 80 wt% based on the total weight of the acrylic copolymer and the refined oil, the acrylic copolymer comprising an acidic monomer and an amide monomer present in a weight ratio of 95:5 to 5:95 wherein the acrylic copolymer is present in an amount of 30 to 200 parts by weight per hundred parts by weight of the base polymer,
  wherein the polymer composition is swellable when treated with an aqueous medium, non-aqueous medium, or both.

18. The polymer composition of claim 17, wherein the acidic monomer is acrylic acid or methacrylic acid, and the amide monomer is acrylamide or methacrylamide, and the weight ratio of the acidic monomer and the amide monomer is 90:10 to 10:90.

19. The polymer composition of claim 17, wherein the liquid dispersed acrylic copolymer comprises acrylic copolymer dispersed in a refined oil and water emulsion.

* * * * *